US010043047B2

(12) United States Patent
Opalsky

(10) Patent No.: US 10,043,047 B2
(45) Date of Patent: Aug. 7, 2018

(54) SYSTEMS AND METHODS FOR READING MACHINE-READABLE MARKS ON RACKS AND RECEPTACLES

(71) Applicant: GEN-PROBE INCORPORATED, San Diego, CA (US)

(72) Inventor: David Opalsky, San Diego, CA (US)

(73) Assignee: GEN-PROBE INCORPORATED, San Diego, CA (US)

( * ) Notice: Subject to any disclaimer, the term of this patent is extended or adjusted under 35 U.S.C. 154(b) by 0 days.

(21) Appl. No.: 15/332,729

(22) Filed: Oct. 24, 2016

(65) Prior Publication Data

US 2017/0235984 A1    Aug. 17, 2017

Related U.S. Application Data

(60) Provisional application No. 62/245,930, filed on Oct. 23, 2015.

(51) Int. Cl.
*G06K 19/00* (2006.01)
*G06K 7/10* (2006.01)
(Continued)

(52) U.S. Cl.
CPC ...... *G06K 7/10811* (2013.01); *G06K 7/10732* (2013.01); *G06K 7/10861* (2013.01);
(Continued)

(58) Field of Classification Search
USPC ........ 235/375, 383, 385, 435, 439, 454, 462
See application file for complete search history.

(56) References Cited

U.S. PATENT DOCUMENTS

2006/0265133 A1* 11/2006 Cocks ............... B01L 3/545
702/19
2014/0175168 A1   6/2014 Hagen et al.

FOREIGN PATENT DOCUMENTS

DE    202012102667 U1    8/2012
DE    202012102669 U1    8/2012

OTHER PUBLICATIONS

PCT, International Preliminary Report on Patentability and Written Opinion, PCT Patent Application No. PCT/US2016/058452, dated Apr. 24, 2018.

* cited by examiner

*Primary Examiner* — Matthew Mikels
(74) *Attorney, Agent, or Firm* — Brian S. Sun; Kyle E. Conklin

(57) ABSTRACT

A sample processing or assay instrument includes a moveable support. The moveable support defines a first pocket configured to receive a first object having a first machine-readable mark. The moveable support defines a second pocket configured to receive a second object having a second machine-readable mark. The moveable support also includes a first fiducial machine-readable mark and a second fiducial machine-readable mark. The instrument also includes an image capture device that captures a first image including the first fiducial machine-readable mark and the first machine-readable mark of the first object. The image capture device captures a second image that includes the second fiducial machine-readable mark and the second machine-readable mark of the second object. The instrument also includes a processor configured to associate information decoded from the first and second machine-readable marks with first and second locations on the moveable support.

22 Claims, 9 Drawing Sheets

(51) Int. Cl.
*G06K 19/06* (2006.01)
*G06K 7/14* (2006.01)
(52) U.S. Cl.
CPC ....... *G06K 7/10881* (2013.01); *G06K 7/1447* (2013.01); *G06K 19/06028* (2013.01)

SYSTEMS AND METHODS FOR READING MACHINE-READABLE MARKS ON RACKS AND RECEPTACLES

CROSS-REFERENCE TO RELATED APPLICATION(S)

This application claims the benefit of U.S. Provisional Application No. 62/245,930, filed Oct. 23, 2015, the entire contents of which are incorporated herein by reference.

FIELD

Embodiments of this disclosure are directed to systems and methods for reading machine-readable marks on sample racks and receptacles, for example, racks and receptacles used to perform molecular assays.

BACKGROUND

An assay instrument performs assays on fluid sample material. For example, in the clinical laboratory context, the analyzer system can be configured to perform multi-step analytical processes (for example, a nucleic acid test (NAT) designed to detect microbe, such as a virus or a bacterium) that involve adding substances (e.g., fluids), such as samples, solid supports, buffers, oil, primers, polymerases, nucleotides, labels, probes, or other reaction fluids, to and/or removing substances from receptacles, agitating receptacles to mix the contents thereof, maintaining and/or altering the temperature of the contents of the receptacles, heating or chilling the contents of the receptacles, altering the concentration of one or more content components of the receptacles, separating or isolating constituent components of the contents of the receptacles, detecting an electromagnetic signal emission (e.g., light) from the contents of the receptacles, deactivating or halting an on-going reaction, or any combination of two or more of such processes.

The assay instrument can be automated to perform the desired analytical process. In such applications, positively matching results of the analytical process to particular sample is needed. To do this, the assay instrument needs to know the locations of sample containers placed onto the instrument. It is also desirable to perform similar tracking of reagents and consumables used to generate results. This disclosure discusses a method to track samples, reagents, and consumables using a hand held or automatic image based barcode reader or similar imaging system. In a typical method of sample tracking, sample containers are labeled with a machine-readable label, e.g., a barcode. The sample container is placed into a holder or rack on an instrument and the instrument either automatically moves the container or monitors the location of a manually moved container. The instrument or operator moves the samples to a location where a built-in barcode reader reads the label on the sample container. The instrument "knows" the location of the sample because the instrument actively moved or monitored the position of a particular sample. The instrument can associate a sample in a particular location or slot in a holder with its barcode and now all processing of the particular sample can be positively tracked to that sample's barcode.

Actuators to move samples in front of an on-board barcode reader or mechanisms to allow the operator to move the samples to the reader while the instrument monitors position can add cost and size to an implementation of an instrument and can have possible negative affects on the reliability of the instrument. The method discussed in this disclosure shows an alternative where a hand-held barcode reader and a specially labeled rack or labeled positions in the instrument allow positive association of a sample with a position in a rack or positive association of a reagent or other consumable with a position in an instrument.

SUMMARY

A method of reading machine-readable marks on a moveable support and objects of a sample instrument includes capturing a first image of the moveable support as the moveable support moves from a first position to a second position using an image capture device. The method also includes determining whether a first fiducial machine-readable mark on the moveable support is in the first image. The method also includes determining, when the first fiducial machine-readable mark is in the first image, whether a first machine-readable mark on an object coupled to the moveable support is in the first image at a predetermined position relative to the first fiducial machine-readable mark. The method further includes decoding, when the first machine-readable mark on the object is in the first image, the first machine-readable mark in the first image. And the method includes associating information decoded from the first machine-readable mark on the object with a first location on the moveable support associated with the first fiducial machine-readable mark.

A sample instrument includes a moveable support configured to move from a first position to a second position. The moveable support defines a first pocket configured to receive a first object having a first machine-readable mark. The moveable support also defines a second pocket configured to receive a second object having a second machine-readable mark. The moveable support includes a first fiducial machine-readable mark containing information that identifies a location of the first fiducial machine-readable mark and a second fiducial machine-readable mark containing information that identifies a location of the second fiducial machine-readable mark. The instrument also includes an image capture device having a field of view that captures a first image. The first image includes the first fiducial machine-readable mark and, when the first object is received within the first pocket, the first machine-readable mark of the first object. The image capture device also captures a second image as the moveable support moves from the first position to the second position. The second image includes the second fiducial machine-readable mark and, when the second object is received within the second pocket, the second machine-readable mark of the second object. The instrument also includes a processor configured to decode the first machine-readable mark and the first fiducial machine-readable mark in the first image. The processor is configured to associate information decoded from the first machine-readable mark with a first location on the moveable support having a predetermined association with the first fiducial machine-readable mark. The processor can also decode the second machine-readable mark and the second fiducial machine-readable mark in the second image. And the processor can associate information decoded from the second machine-readable mark with a second location on the moveable support having a predetermined association with the second fiducial machine-readable mark.

BRIEF DESCRIPTION OF THE DRAWINGS

The accompanying drawings, which are incorporated herein and form a part of the specification, illustrate the embodiments and, together with the description, further serve to explain the principles of the embodiments and to enable a person skilled in the relevant art(s) to make and use the embodiments.

Figure 1:
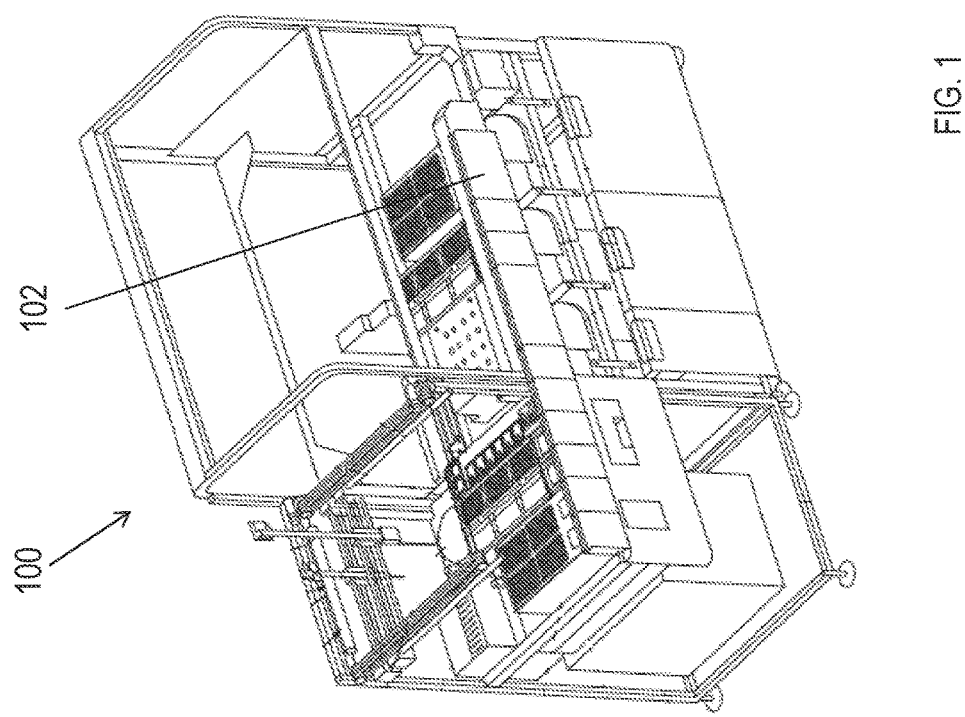
FIG. 1 illustrates a partial, perspective view of an analyzer system that includes a sample bay according to an embodiment.

The features and advantages of the embodiments will become more apparent from the detailed description set forth below when taken in conjunction with the drawings, in which like reference characters identify corresponding elements throughout. In the drawings, like reference numbers generally indicate identical, functionally similar, and/or structurally similar elements.

DETAILED DESCRIPTION

The present invention will now be described in detail with reference to embodiments thereof as illustrated in the accompanying drawings. References to "one embodiment," "an embodiment," "some embodiments," "other embodiments," "an exemplary embodiment," "for example," "an example," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Embodiments described in this application provide systems and methods for reading machine-readable marks (for example, one-dimensional barcodes, two-dimensional barcodes, alphanumerical characters, symbols, or any other suitable machine-readable mark) on movable supports (for example, sample racks, reagent drawers, or consumable drawers) and objects releasably coupled to the moveable supports (for example, sample receptacles, reagent containers, and consumables) that are used in a sample instrument, for example, a sample processing instrument or a sample assay instrument. For example, the assay instrument can be configured to receive one or more moveable supports that releasably hold a plurality of objects each having a machine-readable mark, for example, a one- or two-dimensional barcode. The moveable supports defining a plurality of pockets for receiving the plurality of objects, and having at least one machine-readable fiducial mark that corresponds to each pocket defined by the moveable support. The location of each of the at least one machine-readable fiducial mark on the moveable support is known (i.e., predetermined). The assay instrument can include an image capture device, for example, a camera, configured to capture an image that includes the machine-readable marks on the sample rack and sample receptacles. The system also includes a processor that processes the captured images to identify and decode machine-readable marks in the captured images. The processor can also associate information from the identified and decoded machine-readable marks on the sample rack with information from the corresponding identified and decoded machine-readable marks on the sample receptacles. Such systems and methods for reading machine-readable marks on sample racks and sample receptacles can be used for performing assays on fluid sample material and for identifying the contents of the sample receptacles, for example, patient information (e.g., patient identification numbers).

In this application, a "sample instrument" is a sample processing instrument or a sample assay instrument. In this application, a "sample assay instrument" is any instrument capable of analyzing a sample and rendering a result. For example, any instrument capable of performing a hybridization assay, an amplification assay, a sequencing assay, or an immunoassay on a sample is an assay instrument. Assay instruments can perform an assay directly on a sample without any sample processing, or an assay instrument can further process the sample before performing an assay. Samples that can require some form of sample processing before subjecting the samples to the steps of an assay include, in some embodiments, cell samples, tissue samples, stool samples, mucus samples, semen samples, cerebrospinal fluid samples, blood samples, bone marrow samples, serum samples, urine samples, bile samples, respiratory samples, sputum samples, and exosome samples, among others. Exemplary assay instruments include the Tigris® and Panther® systems (Hologic, Inc., San Diego, Calif.). In this disclosure, a "sample processing instrument" is any instrument capable of performing a processing step on a sample contained within a receptacle before performing an assay on the sample, but not capable of analyzing a sample and rendering a result. Exemplary sample processing instruments include the Tomcat® instrument (Hologic, Inc., San Diego, Calif.). In this disclosure, a "sample" is any material to be analyzed, regardless of the source. The material may be in its native form or any stage of processing (e.g., the material may be chemically altered or it may be one or more components of a sample that have been separated and/or purified from one or more other components of the sample). A sample may be obtained from any source, including, but not limited to, an animal, environmental, food, industrial or water source. Animal samples include, but are not limited to, peripheral blood, plasma, serum, bone marrow, urine, bile, mucus, phlegm, saliva, cerebrospinal fluid, stool, biopsy tissue including lymph nodes, respiratory tissue or exudates, gastrointestinal tissue, cervical swab samples, semen or other body or cellular fluids, tissues, or secretions. Samples can be diluted or contained within a receptacle containing diluents, transport media, preservative solution, or other fluids. As such, the term "sample" is intended to encompass samples contained within a diluent, transport media, and/or preservative or other fluid intended to hold a sample.

Figure 2:
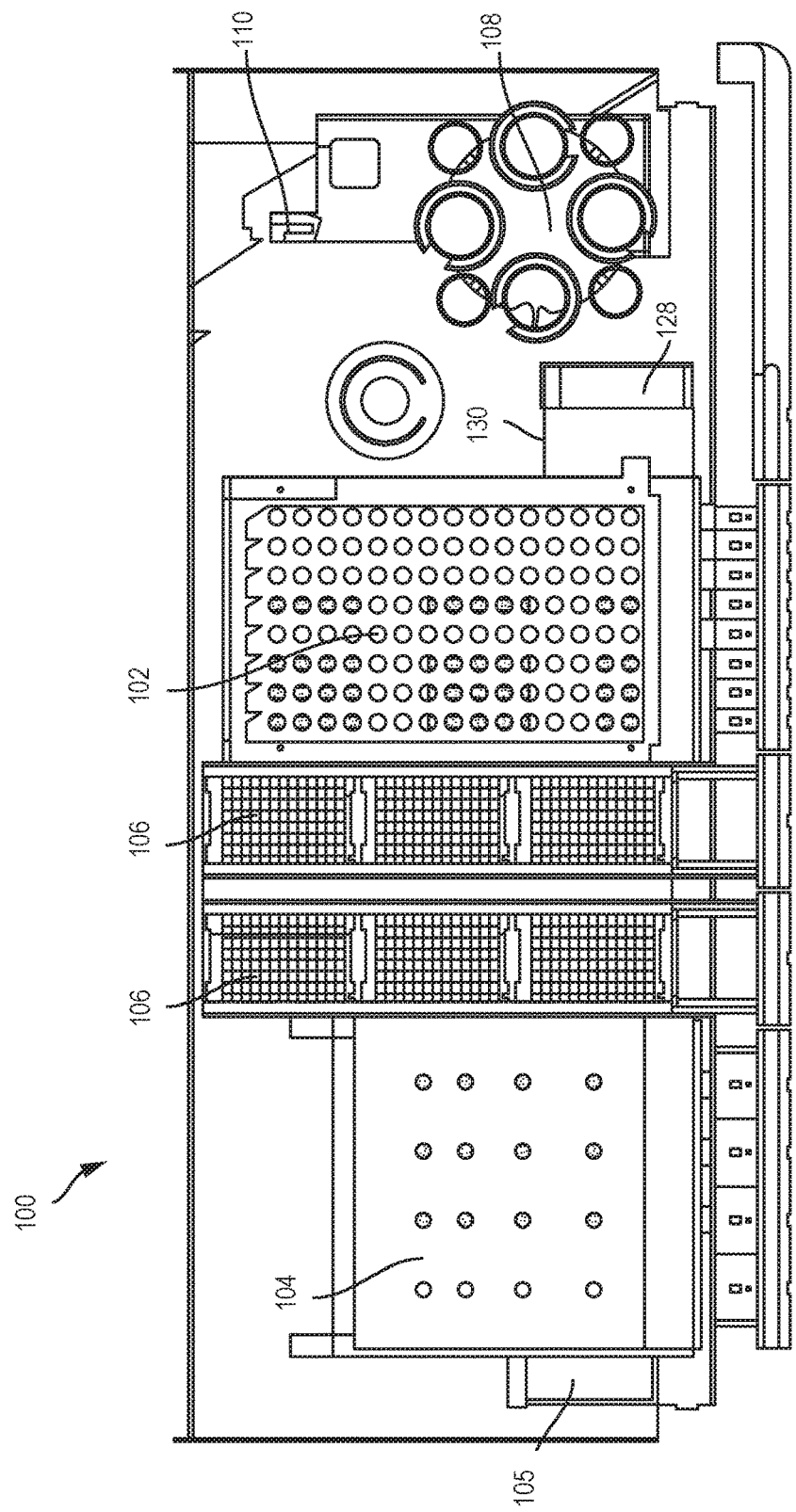
FIG. 2 illustrates a cross-sectional plan view of the analyzer system of FIG. 1 according to an embodiment.

FIGS. 1 and 2 illustrate a perspective view and a plan, cross-sectional view, respectively, of an exemplary sample instrument 100, namely, a sample assay instrument that performs assays on a sample. In some embodiments, sample assay instrument 100 is configured to perform a multi-step analytical process (for example, a nucleic acid test (NAT) designed to detect a microbe, such as a virus or a bacterium) or other chemical, biochemical or biological processes. Exemplary process steps include, for example, adding substances (e.g., fluids), such as samples, solid supports, buffers, oil, primers, polymerases, nucleotides, labels, probes, or other reaction fluids, to and/or removing substances from receptacles, agitating receptacles to mix the contents thereof, maintaining and/or altering the temperature of the contents of the receptacles (for example, using heated incubators configured to receive a plurality of reaction receptacles and maintain the receptacles in an elevated temperature environment), heating or chilling the contents of the receptacles (for example, using temperature ramping stations configured raise the temperature of the contents of reaction receptacles or chilling modules configured to reduce the temperature of the contents of the receptacles), altering the concentration of one or more content components of the receptacles, separating or isolating constituent components of the contents of the receptacles (for example, using magnetic separation wash stations configured to isolate a target nucleic acid immobilized on a magnetically-responsive solid support from the contents of the receptacle), detecting an electromagnetic signal emission (for example, light) from the contents of the receptacles (for example, using detector configured to detect a signal (e.g., an optical signal) emitted by the contents of the reaction receptacle), deactivating or halting an on-going reaction, or any combination of two or more of such processes. Fluid sample material may include, for example, urine, blood, plasma, sputum, saliva, mucus, pus, seminal fluid, amniotic fluid, cerebrospinal fluid, synovial fluid, and cultures.

In some embodiments, samples are introduced into sample assay instrument 100 via a sample bay 102. FIG. 2 illustrates a cross-sectional, plan view of sample assay instrument 100 according to an embodiment. As shown in FIG. 2, sample assay instrument 100 includes sample bay 102 configured to receive a plurality of sample racks, which are described further below. In some embodiments, sample assay instrument 100 also includes a reagent bay 104. Reagent bay 104 is configured to store one or more containers of reagents used during a multi-step analytical process. In some embodiments, sample assay instrument 100 includes a reader 105, for example, an image capture device or a laser barcode reader, configured to read machine-readable marks, for example, one- or two-dimensional barcodes, on the reagent containers stored on a moveable drawer within reagent bay 104. In some embodiments, sample assay instrument 100 includes one or more moveable tip drawers 106 configured to store a plurality of tips used by a fluid transfer device (not shown in FIG. 2) of sample assay instrument 100. In some embodiments, sample assay instrument 100 includes a target capture reagent carousel 108 configured to support and rotate one or more containers of a target capture reagent (TCR). In some embodiments, sample assay instrument 100 includes a reader 110, for example, an image capture device or laser barcode reader, configured to read machine-readable marks, for example, one- or two-dimensional barcodes, on TCR containers on TCR carousel 108.

Figure 3:
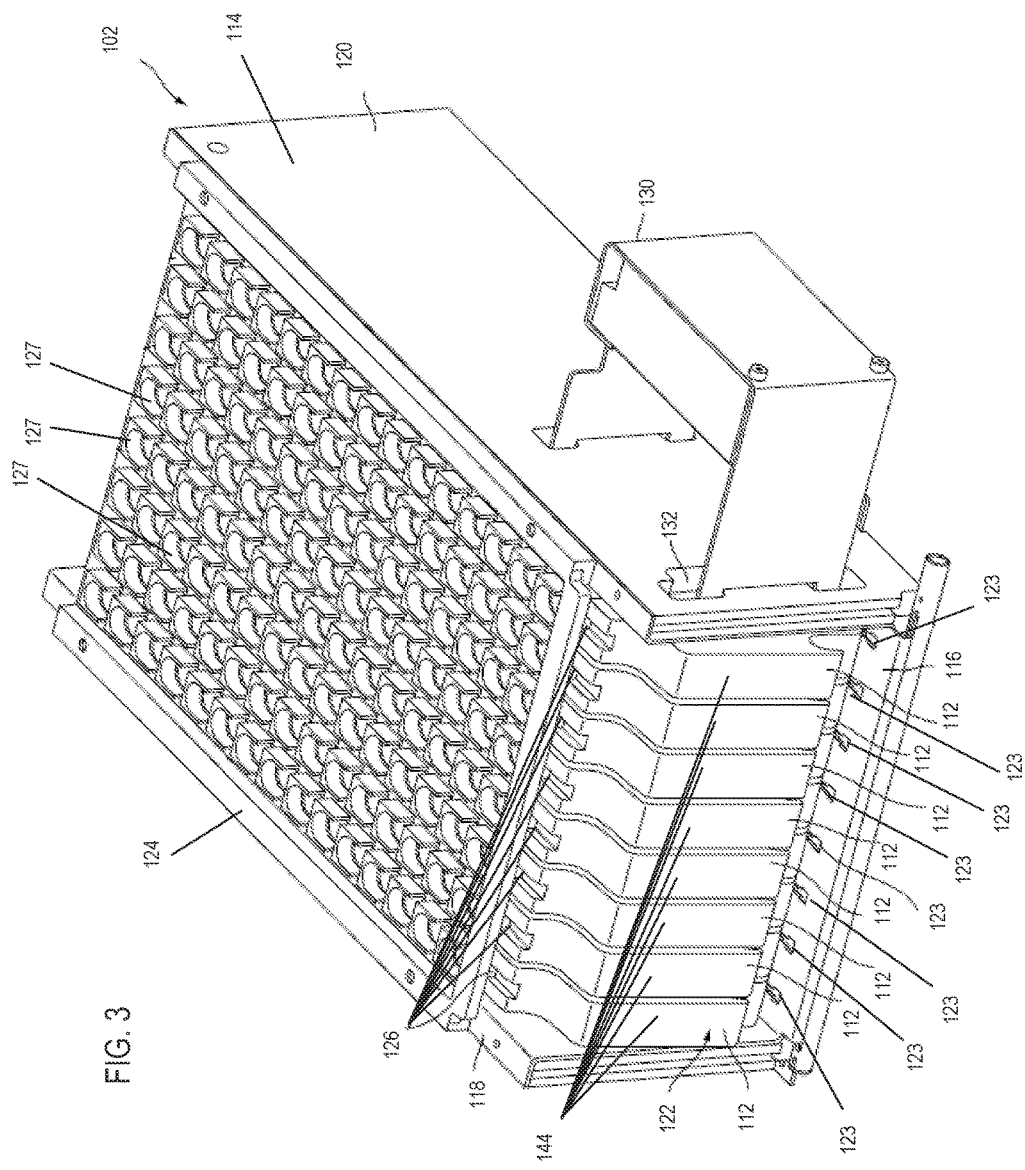
FIG. 3 illustrates a front perspective view of a sample bay according to an embodiment.

FIG. 3 illustrates a front perspective view of sample bay 102 according to an embodiment. Sample bay 102 is configured to receive a plurality of sample racks 112 along defined lanes within sample bay 102. Sample racks 112 each support a plurality of sample receptacles (not shown in FIG. 3) that each contain a sample. For example, as shown in FIG. 3, sample bay 102 is configured to receive eight sample racks 112 that move along defined lanes within sample bay 102. In other embodiments, sample bay 102 is configured to receive less than or more than eight sample racks 112.

Sample bay 102 includes a housing 114 that defines an interior compartment that receives sample racks 112. Housing 114 can be rectangular as shown FIG. 3 or any other suitable shape. In some embodiments, housing 114 includes a base 116 that is, for example, planar and rectangular. Housing 114 also includes a first sidewall 118 and a second sidewall 120 extending from opposing sides of base 116, and a back wall (not shown in FIG. 3) extending from a back side of base 116 between first and second sidewalls 118 and 120. Housing 114 has an opening 122 at its front end to allow sample racks 112 to be inserted into and removed from the compartment defined by housing 114.

Housing 114 defines a plurality of lanes along which sample racks 112 move, for example, eight lanes as shown in FIG. 3. In some embodiments, base 116 includes a plurality of guides 123 that define the lanes of housing 114. Guides 123 can be protrusions that extend from base 116 and are configured to operatively mate with corresponding recesses of sample racks 112. Guides 123 can help ensure that sample racks 112 are accurately and repeatedly positioned in the defined lanes of housing 114 as sample racks 112 move within the compartment defined by sample bay 102. As shown in FIG. 3, the lanes are straight and extend from the front end of housing 114 to the back end of housing 114.

In some embodiments, housing 114 also includes a top panel 124. In some embodiments, top panel 124 includes a plurality of guides 126 that define, along with guides 123, the lanes in which sample racks 112 move. Guides 126 can be protrusions that extend from top panel 124 toward base 116 and that are configured to operatively mate with corresponding recesses on sample racks 112. In some embodiments, top panel 124 defines a plurality of sample receptacle access openings 127, which in some embodiments as shown in FIG. 3, are arranged in a rectangular array of rows and columns. Each column of openings 126 is aligned with a respective sample rack 112, providing assay instrument 101, for example, easy access to receptacles held by sample racks 112.

Sample bay 102 also includes an image capture device 128 configured to capture images of machine-readable marks (for example, one-dimensional barcodes, two-dimensional barcodes, alphanumerical characters, symbols, and any other suitable machine-readable mark) on sample racks 112, and to capture images of machine-readable marks (for example, one-dimensional barcodes, two-dimensional barcodes, alphanumerical characters, symbols, and any other suitable machine-readable mark) on sample receptacles supported by sample racks 112. In some embodiments, as shown in FIG. 3, sample bay 102 includes an image capture device support 130 configured to support image capture device 128 and fixedly coupled to housing 114. Image capture device 128 is coupled to image capture device support 130 and, thus, fixedly coupled to housing 114. As shown in FIG. 3, image capture device support 130 is coupled to housing 114, for example, fixedly coupled to side wall 120. In some embodiments, when viewed from above, image capture device support 130 is substantially U-shaped and forms a compartment sized to receive and support image capture device 128. And image capture device 128 is coupled to image capture device support 130, fixing the position of image capture device 128 relative to housing 114 in some embodiments.

Side wall 120 can define an opening 132 extending into the interior compartment defined by housing 114 such that image capture device 128 can read labels on sample racks 112 within housing 114 through opening 132. In some embodiments, image capture device 128 is configured to read machine-readable marks as sample racks 112 are inserted into or removed from housing 114. In other embodiments, image capture device 128 is configured to read machine-readable marks after sample racks 112 are fully inserted into housing 114.

In some embodiments, image capture device 128 is disposed outside of housing 114 and spaced from opening 132 as shown in FIG. 3. In other embodiments (not shown), image capture device 128 is disposed outside of housing 114 and directly adjacent opening 132, or image capture device 128 is disposed within housing 114. In yet other embodiments, image capture device 128 is a hand-held device separate from housing 114 that a user manually operates to read machine-readable marks on sample racks 112 and receptacles held by racks 112 before being inserted within sample bay 102.

In some embodiments, as shown in FIG. 3, sample bay 102 includes a light source, for example, a strobe light, configured to illuminate the interior of housing 114. For example, light source can illuminate machine-readable marks on sample racks 112 and sample receptacles held by sample racks 112 within housing 114. As shown in FIG. 3, for example, light source is near image capture device 128 and coupled to image capture device support 130. In some embodiments, light source includes an array of LEDs. In some embodiments (not shown), light source is disposed inside housing 114 or at any other suitable location. In some embodiments, light source is embodied within image capture device 128.

Figure 9:
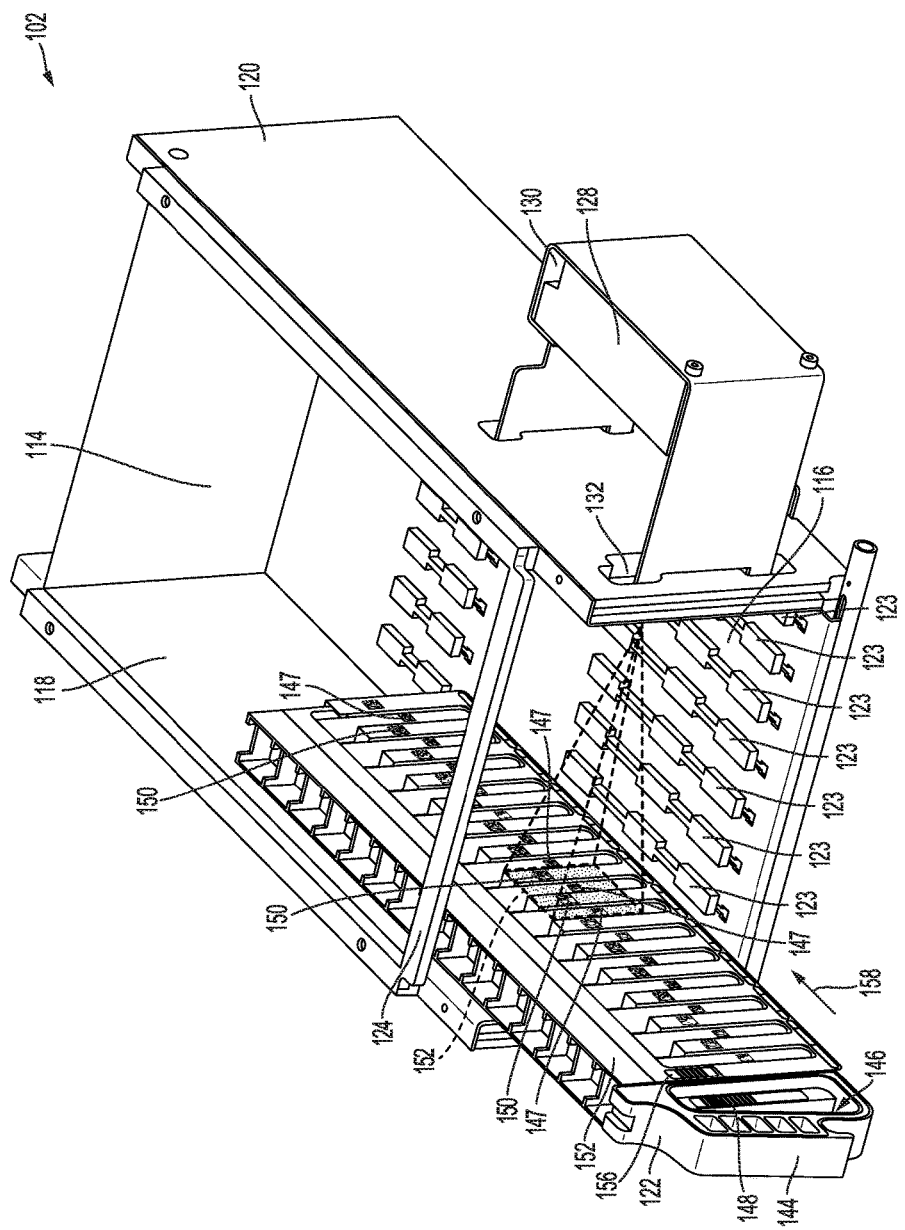
FIG. 9 illustrates a front perspective view of a sample bay with a rack partially inserted into a housing of the sample bay according to an embodiment.

As best seen in FIGS. 3 and 9, each sample rack 112 can include a handle 144 configured to allow a user to grasp and manually move sample rack 112 in some embodiments. For example, a user can grasp handle 144 to insert or remove sample rack 112 from housing 114 of sample bay 102. In some embodiments, as best seen in FIG. 9, handle 144 defines an opening 146 that is configured to allow a user's fingers to pass through. And in some embodiments, opening 146 allows the optical path along which image capture device 128 captures an image to pass through one sample rack 112 to read a machine-readable mark on another sample rack 112 positioned on the other side of opening 146 from image capture device 128.

In some embodiments, as shown in FIG. 9, sample rack 112 includes a rack identifier that provides unique rack-identifying information, for example, a rack identification number. In some embodiments (not shown), the rack identifier is an RFID tag. In such RFID embodiments, sample bay 102 includes an RFID reader configured to interrogate the RFID tag when sample rack 112 is within sample bay 102. In other embodiments (as shown in FIG. 9), the rack identifier is a machine-readable mark 148, for example, a one- (as shown in FIG. 9) or two-dimensional barcode. Image capture device 128 can be configured to capture an image that includes rack-identifying machine-readable mark 148. Rack-identifying, machine-readable mark 148 can be positioned near handle 144 of sample rack 112, as shown in FIG. 9, in some embodiments.

FIGS. 4-8 illustrate various embodiments of sample rack 112, sample receptacles 136, and the field of view of image capture device 128.

Figure 4:
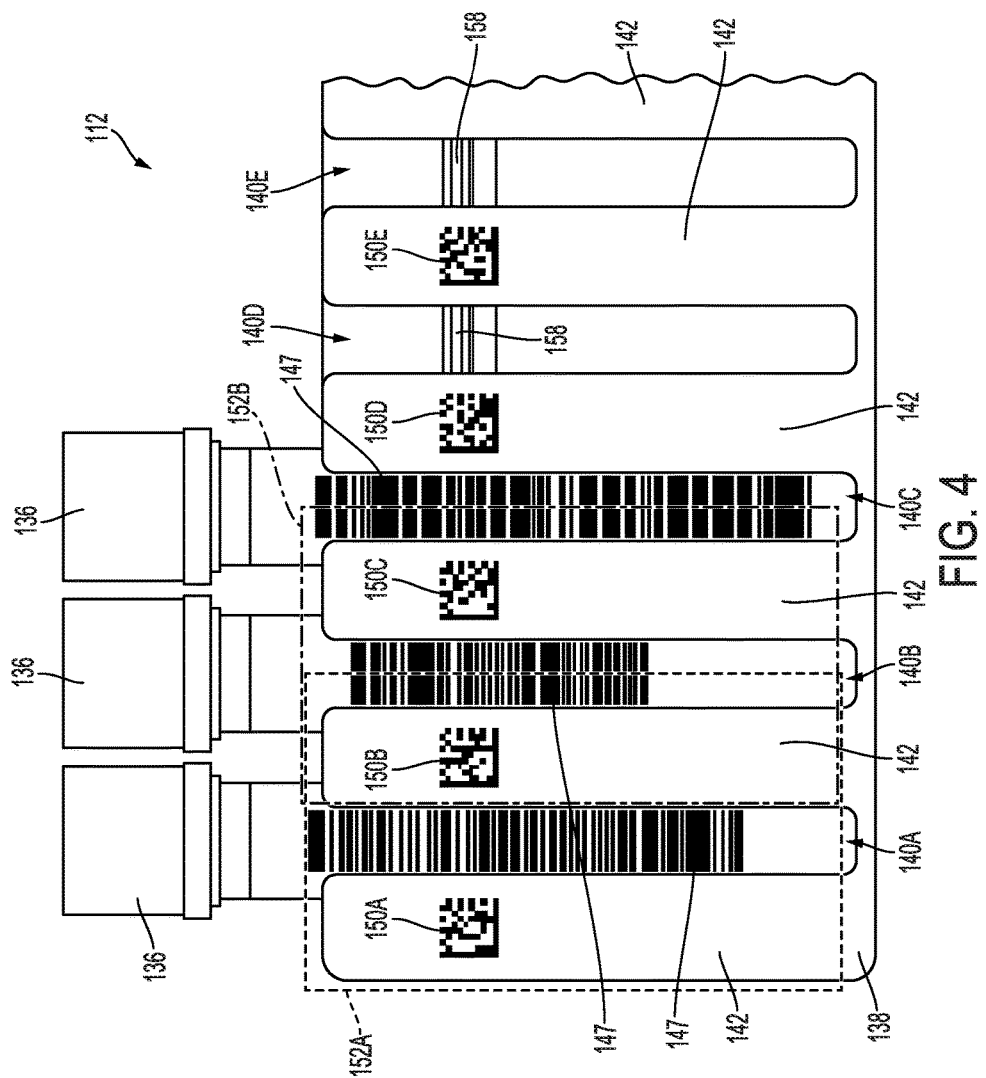
FIG. 4 illustrates a partial side view of a sample rack supporting sample receptacles according to an embodiment.
Figure 5:
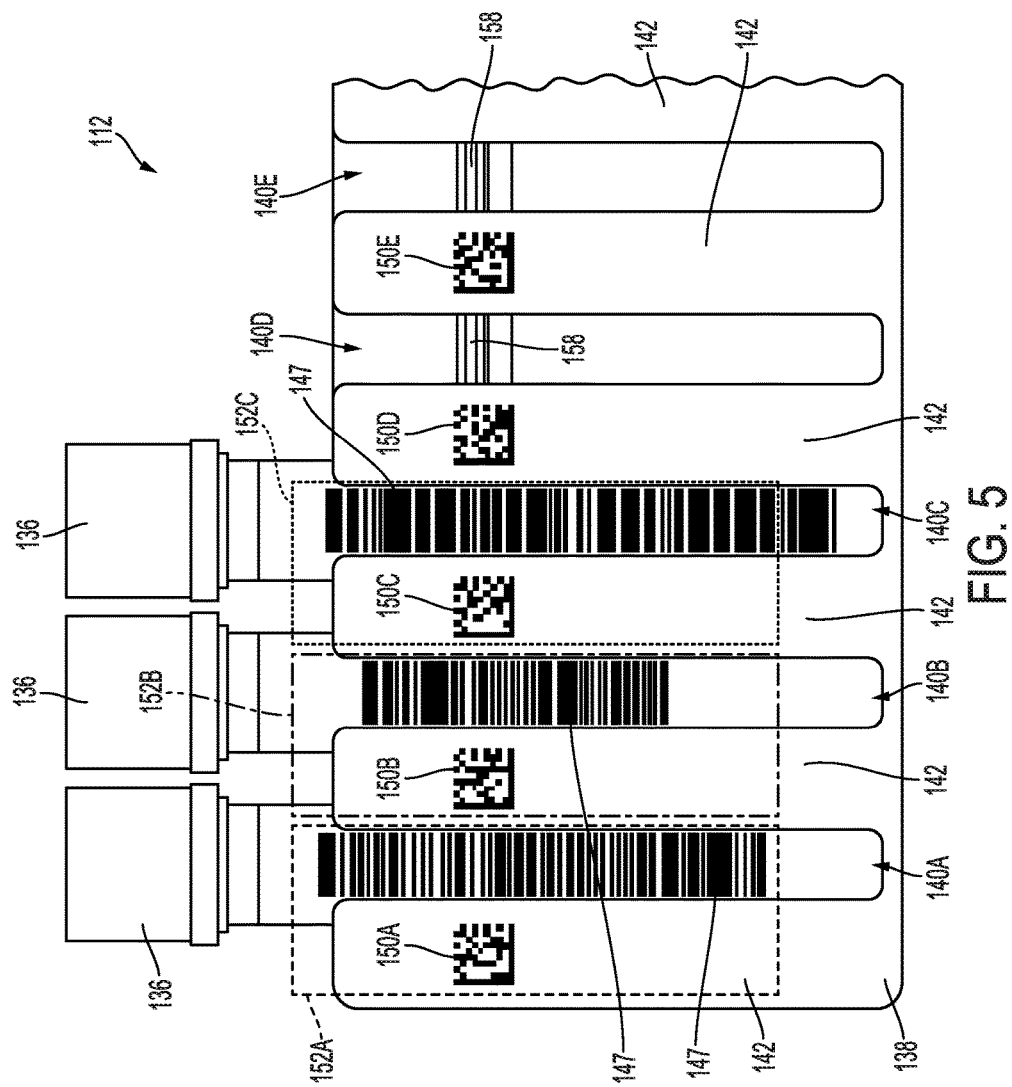
FIG. 5 illustrates a partial side view of a sample rack supporting sample receptacles according to another embodiment.
Figure 6:
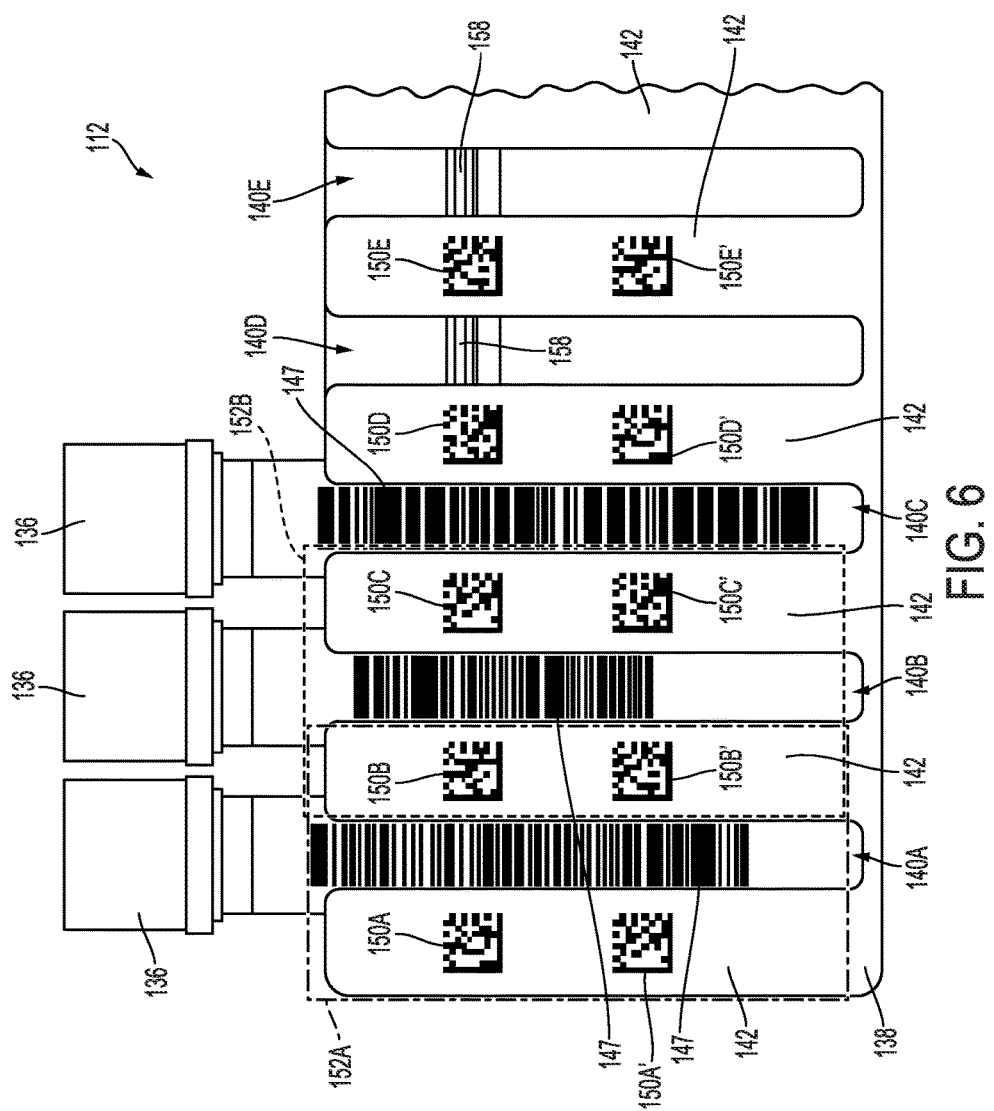
FIG. 6 illustrates a partial side view of a sample rack supporting sample receptacles according to yet another embodiment.
Figure 7:
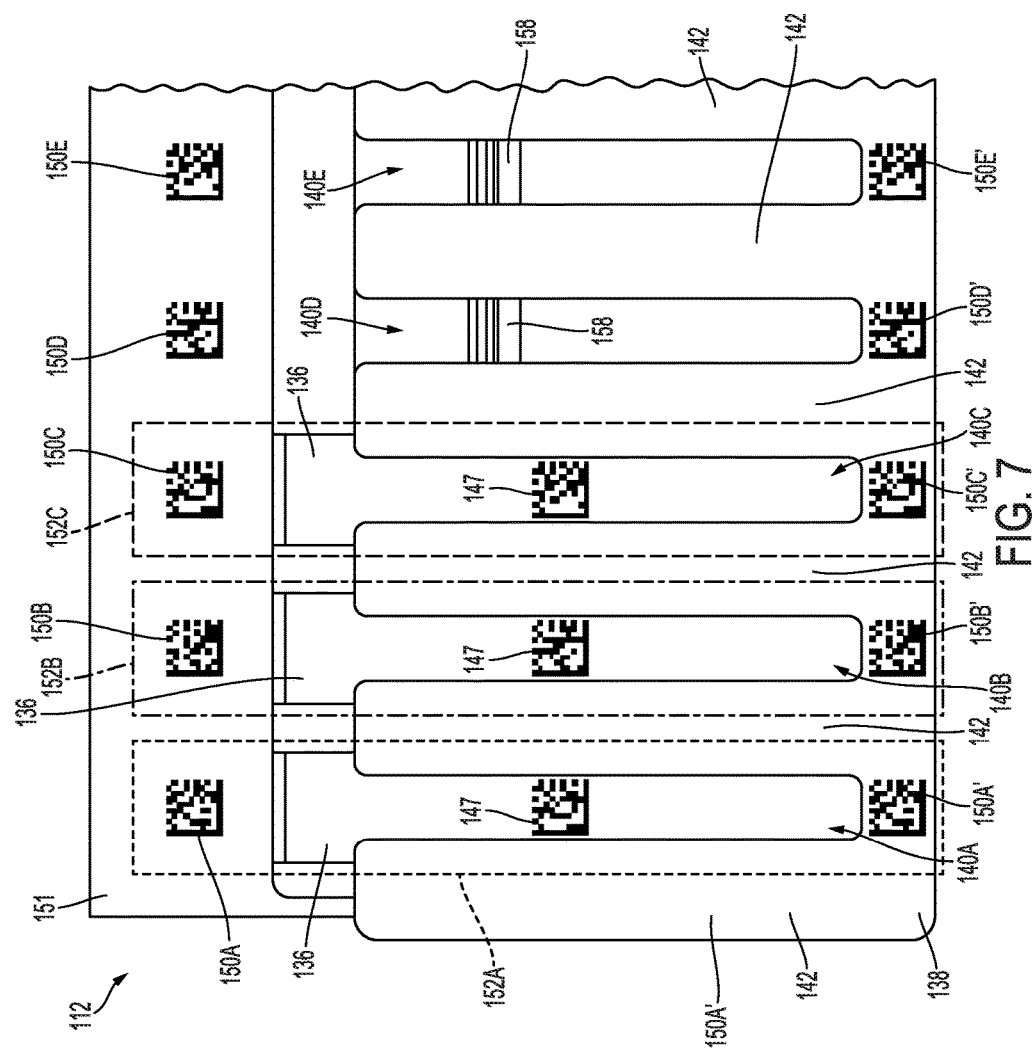
FIG. 7 illustrates a partial side view of a sample rack supporting sample receptacles according to another embodiment.
Figure 8:
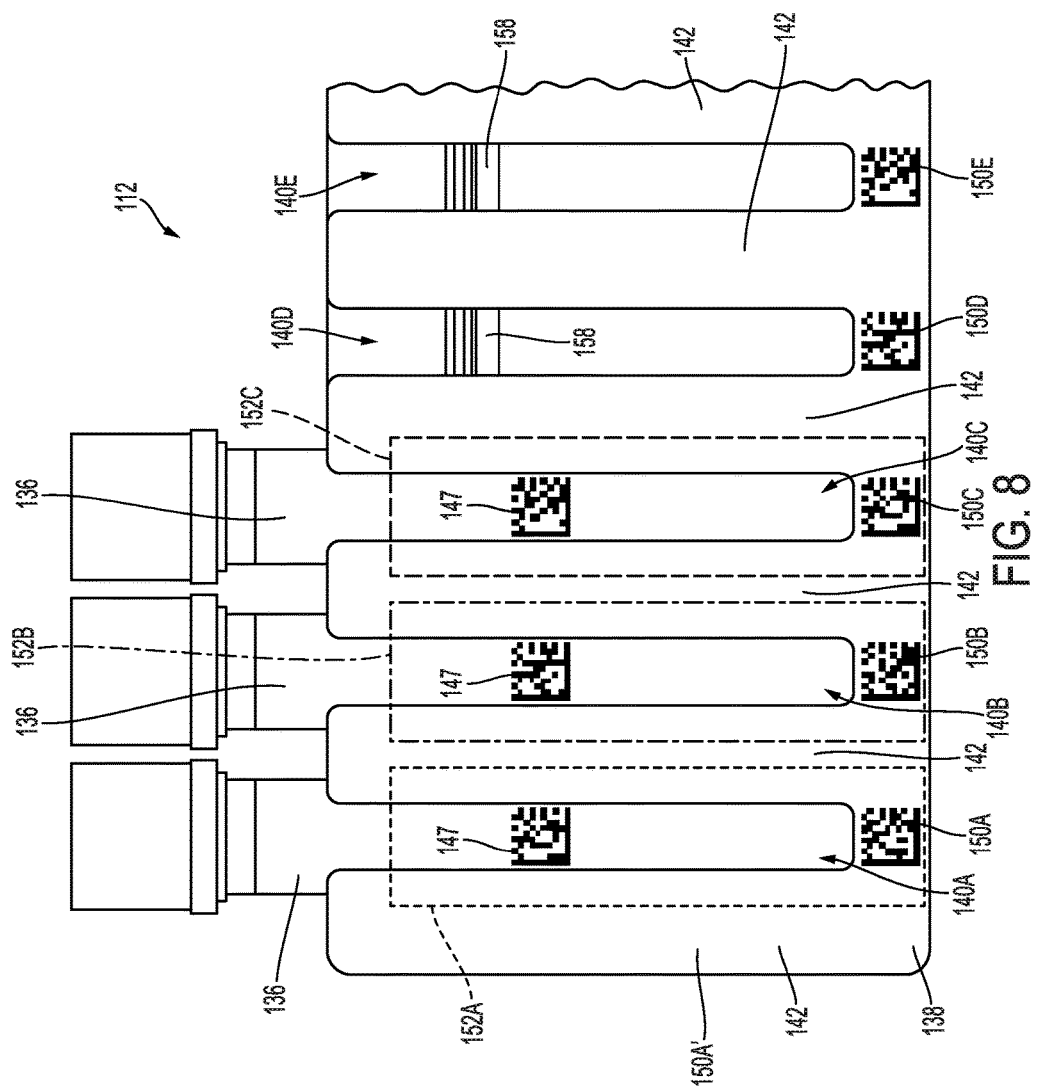
FIG. 8 illustrates a partial side view of a sample rack supporting sample receptacles according to yet another embodiment.

Referring to FIG. 4, sample rack 112 is configured to hold a plurality of sample receptacles 136. For example, sample rack 112 can be configured to hold fifteen sample receptacles 136. Sample receptacles 136 can be any type of fluid container, including, for example, a tube, vial, cuvette, cartridge, microtiter plate, etc. that is configured to contain a sample at any point during processing of the sample. In some embodiments, each sample receptacle 136 supported by sample rack 112 includes at least one machine-readable mark 147. Machine-readable mark 147 can be, (for example, one-dimensional barcodes (as shown in FIGS. 4, 5, and 6), two-dimensional barcodes (as shown in FIGS. 7 and 8), alphanumerical characters, symbols, and any other suitable machine-readable mark. One-dimensional barcodes express information in one direction, for example, either the horizontal direction or the vertical direction. Examples of one-dimensional barcodes include Code 39 codes, Code 128 codes, Interleaved 2 of 5 codes, and Codabar codes. Two-dimensional barcodes express information in two directions, for example, in the horizontal and vertical directions, and include stacked barcodes and matrix barcodes. Examples of two-dimensional barcodes include Aztec codes, PDF417 codes, MaxiCodes, Codablock codes, Data Matrix codes, and QR codes. Two-dimensional barcodes can improve decoding accuracy and increase the amount of information contained within the barcode relative to a one-dimensional barcode. In some embodiments, machine-readable mark 147 for each receptacle 136 contains one or more of the following items of information: patient information such as a unique patient identifier (for example, patient name or patient identification number), patient metadata (for example, date of birth, age, sex, height, or weight), medical history, or any other desired patient information; and sample information such as the healthcare provider requesting the assay, the sample type, the date the sample was collected, the collection site, the type of assays to be performed, assay test results, and other suitable information.

As shown in FIG. 4, sample rack 112 includes a base 138 that defines a plurality of pockets 140 for closely receiving sample receptacles 136. Pockets 140 can be separated from each other by a vertical dividing wall 142 in some embodiments. As shown in FIG. 4, vertical dividing walls 142 are configured to form gaps there between such that, when a receptacle 136 is placed within a pocket 140, machine-readable mark 147 on sample receptacle 136 is visible to image capture device 128.

Sample rack 112 includes at least one fiducial machine-readable mark 150 and, in some embodiments, at least one fiducial machine-readable mark for each pocket 140 of sample rack 112. Fiducial machine-readable marks 150 can be, for example, one-dimensional barcodes, two-dimensional barcodes (as shown in FIGS. 4-8), alphanumerical characters, symbols, and any other suitable machine-readable mark. Two-dimensional barcodes can improve decoding accuracy and increase the amount of information contained within fiducial machine-readable mark 150. In some embodiments, each fiducial machine-readable mark 150 contains information that can be used to identify the location of the fiducial machine-readable mark 150 on sample rack 112. For example, each fiducial machine-readable mark 150 can contain unique information, for example, a unique identification number, value, or letter, that has a known association with a specific location on sample rack 112.

These associations between the fiducial machine-readable marks 150, including, for example, unique information contained in the fiducial machine-readable marks 150, and the specific locations on sample rack 112 can be stored in a memory of sample assay instrument 100 in some embodiments.

In some embodiments, fiducial machine-readable marks 150 are located on the outer surface of dividing walls 142 that separate adjacent pockets 140 from each other. In other embodiments (described further below), fiducial machine-readable marks 150 are located on a cover configured to fit over the top of sample receptacles 136 held within pockets 140 of sample rack 112. In other embodiments (described further below), fiducial machine-readable marks 150 are located on a portion of base 138 of sample rack 112 that is below pockets 140 of sample rack 112.

In some embodiments, as shown in FIGS. 4 and 5, sample rack 112 can include one fiducial machine-readable mark 150 on a left and right side of each pocket 140. And in some embodiments, as shown in FIGS. 4 and 5, fiducial machine-readable marks 150 are linearly (e.g., horizontally) aligned. In some embodiments, as shown in FIG. 6, sample rack 112 can include two vertically aligned fiducial machine-readable marks 150 on a left and right side of each pocket 140. In some embodiments, as shown in FIG. 7, sample rack 112 can include one fiducial machine-readable mark 150 on a top and bottom side of each pocket 140. And in some embodiments, as shown in FIG. 8, sample rack 112 can include one fiducial machine-readable mark 150 below and vertically aligned with each pocket 140.

Sample rack 112 can also include a machine-readable mark 158 within each pocket 140 of sample rack 112 in some embodiments. Machine-readable marks 158 can be, for example, one-dimensional barcodes (as shown in FIGS. 4-8), two-dimensional barcodes, alphanumerical characters, symbols, and any other suitable machine-readable mark. Machine-readable marks 158 are positioned within each pocket 140 such that they are visible to image capture device 128 when a sample receptacle 136 is not received within the corresponding pocket 140. For example, as shown in FIG. 4, empty-pocket identifying machine-readable marks 158 are shown in pockets 140D and 140E of sample rack 112 because these two pockets 140D and 140E are not holding a sample receptacle 136.

The positions of machine-readable marks 147 on sample receptacles 136 relative to respective fiducial machine-readable mark(s) 150 when sample receptacles 136 are placed in pockets 140 are known, and the positions of empty-pocket identifying machine-readable marks 158 on sample rack 112 relative to respective fiducial machine-readable mark(s) 150 are known. These known relative positions can be saved in a memory of sample assay instrument 100.

In some embodiments, as shown in FIG. 4, image capture device 128 has a field of view sufficient to capture images that include (1) at least one fiducial machine-readable mark 150 and (2) at least one of (a) at least one machine-readable mark 147 on at least one sample receptacle 136 received in respective pockets 140 and (b) at least one empty-pocket identifying machine-readable mark 158 in respective pockets 140. For example, as shown in FIG. 4, image capture device 128 has a field of view that captures an image that includes (1) a pair of fiducial machine-readable marks 150 (one mark 150 on a left side of a respective pocket 140 and one mark 150 on a right side of a respective pocket 140) and (2) either a machine-readable mark 147 on the sample receptacle 136 received in the respective pocket or an empty-pocket identifying machine-readable mark 158 in the respective pocket 140 if the respective pocket 140 is empty. As shown in FIG. 4, image capture device 128 has a field of view sufficient to capture image 152A that includes (1) fiducial machine-readable mark 150A on a left side of pocket 140A, (2) fiducial machine-readable mark 150B on a right side of pocket 140A, and (3) machine-readable mark 147 on sample receptacle 136 in pocket 140A. Image capture device 128 has a field of view sufficient to subsequently capture image 152B (as sample rack 112 is inserted within sample bay 102) that includes (1) fiducial machine-readable mark 150B on a left side of pocket 140B, (2) fiducial machine-readable mark 150C on a right side of pocket 140B, and (3) machine-readable mark 147 on sample receptacle 136 in pocket 140B. Image capture device 128 can subsequently capture similar images of fiducial machine-readable marks 150C, 150D, 150E, etc. and machine-readable marks 147 on sample receptacles 136 in pockets 140C, 140D, 140E, etc.

In some embodiments, as shown in FIG. 5, image capture device 128 has a field of view that captures an image that includes (1) only one fiducial machine-readable mark 150 (e.g., mark 150 on a left side of a respective pocket 140) and (2) either a machine-readable mark 147 on the sample receptacle 136 received in the respective pocket 140 or an empty-pocket identifying machine-readable mark 158 in the respective pocket 140 if the respective pocket 140 is empty. As shown in FIG. 5, image capture device 128 has a field of view sufficient to capture image 152A that includes (1) fiducial machine-readable mark 150A on a left side of pocket 140A, and (2) machine-readable mark 147 on sample receptacle 136 in pocket 140A (or machine-readable mark 158 if no sample receptacle 136 is in pocket 140A). Image capture device 128 has a field of view sufficient to subsequently capture image 152B (as sample rack 112 is inserted within sample bay 102) that includes (1) fiducial machine-readable mark 150B on a left side of pocket 140B, and (2) machine-readable mark 147 on sample receptacle 136 in pocket 140B (or machine-readable mark 158 if no sample receptacle 136 is in pocket 140B). Image capture device 128 has a field of view sufficient to subsequently capture image 152C (as sample rack 112 is further inserted within sample bay 102) that includes (1) fiducial machine-readable mark 150C on a left side of pocket 140C, and (2) machine-readable mark 147 on sample receptacle 136 in pocket 140C (or machine-readable mark 158 if no sample receptacle 136 is in pocket 140C). Image capture device 128 can subsequently capture similar images of fiducial machine-readable marks 150D, 150E, etc. and machine-readable marks 147 on sample receptacles 136 in pockets 140D, 140E, etc (or machine-readable marks 158 if no sample receptacles 136 are in pocket 140D, 140E, etc.).

As shown in FIG. 6, image capture device 128 has a field of view sufficient to capture an image that includes (1) a pair of fiducial machine-readable marks 150 on a left side of a respective pocket 140 and a pair of fiducial machine-readable marks 150 on a right side of the respective pocket 140) and (2) either a machine-readable mark 147 on the sample receptacle 136 received in the respective pocket or an empty-pocket identifying machine-readable mark 158 in the respective pocket 140 if the respective pocket 140 is empty. As shown in FIG. 6, image capture device 128 has a field of view sufficient to capture image 152A that includes (1) fiducial machine-readable marks 150A and 150A' on a left side of pocket 140A, (2) fiducial machine-readable marks 150B and 150B' on a right side of pocket 140A, and (3) machine-readable mark 147 on sample receptacle 136 in pocket 140A. Image capture device 128 has a field of view sufficient to subsequently capture image 152B (as sample rack 112 is inserted within sample bay 102) that includes (1) fiducial machine-readable marks 150B and 150B' on a left side of pocket 140B, (2) fiducial machine-readable marks 150C and 150C' on a right side of pocket 140B, and (3) machine-readable mark 147 on sample receptacle 136 in pocket 140B. Image capture device 128 can subsequently capture similar images of fiducial machine-readable marks 150C, 150C', 150D, 150D', 150E, 150E', etc. and machine-readable marks 147 on sample receptacles 136 in pockets 140C, 140D, 140E, etc (or machine-readable marks 158 if no sample receptacles 136 are in pocket 140C, 140D, 140E, etc.).

As shown in FIG. 7, image capture device 128 has a field of view sufficient to capture images that each include (1) a pair of fiducial machine-readable marks 150 (one mark 150 on a top side of a respective pocket 140 and one mark 150 on a bottom side of a respective pocket 140) and (2) either a machine-readable mark 147 on the sample receptacle 136 received in the respective pocket or an empty-pocket identifying machine-readable mark 158 in the respective pocket 140 if the respective pocket 140 is empty. As shown in FIG. 7, image capture device 128 has a field of view sufficient to capture image 152A that includes (1) fiducial machine-readable mark 150A on a top side of pocket 140A, (2) fiducial machine-readable mark 150A' on a bottom side of pocket 140A, and (3) machine-readable mark 147 on sample receptacle 136 in pocket 140A. Image capture device 128 has a field of view sufficient to subsequently capture image 152B (as sample rack 112 is inserted within sample bay 102) that includes (1) fiducial machine-readable mark 150B on a top side of pocket 140B, (2) fiducial machine-readable mark 150B' on a bottom side of pocket 140B, and (3) machine-readable mark 147 on sample receptacle 136 in pocket 140B. Image capture device 128 has a field of view sufficient to subsequently capture image 152C (as sample rack 112 is further inserted within sample bay 102) that includes (1) fiducial machine-readable mark 150C on a top side of pocket 140C, (2) fiducial machine-readable mark 150C' on a bottom side of pocket 140C, and (3) machine-readable mark 147 on sample receptacle 136 in pocket 140C (or machine-readable mark 158 if no sample receptacle 136 is in pocket 140C). Image capture device 128 can subsequently capture similar images of fiducial machine-readable marks 150D, 150D', 150E, 150E', etc. and machine-readable marks 147 on sample receptacles 136 in pockets 140D, 140E, etc (or machine-readable marks 158 if no sample receptacles 136 are in pocket 140D, 140E, etc.).

As shown in FIG. 7, sample rack 112 includes a cover 151 configured to be releasably secured to base 138 of sample rack 112 in some embodiments. In some embodiments, fiducial machine-readable marks 150A-150E are disposed on cover 151, and fiducial machine-readable marks 150A'-150E' are disposed on a portion 154 of base 138 of sample rack 112 that is below pockets 140. In some embodiments, cover 151 also includes a machine-readable mark 156, for example, a one- (as shown in FIG. 9) or two-dimensional barcode. Label 156 is configured to be used to determine whether cover 151 is coupled to base 138 and/or positioned properly relative to base 138.

As shown in FIG. 8, image capture device 128 has a field of view sufficient to capture image 152A that includes (1) fiducial machine-readable mark 150A on a bottom side of pocket 140A, and (2) machine-readable mark 147 on sample receptacle 136 in pocket 140A (or machine-readable mark 158 if no sample receptacle 136 is in pocket 140A). Image capture device 128 has a field of view sufficient to subsequently capture image 152B (as sample rack 112 is inserted within sample bay 102) that includes (1) fiducial machine-readable mark 150B on a bottom side of pocket 140B, and (2) machine-readable mark 147 on sample receptacle 136 in pocket 140B (or machine-readable mark 158 if no sample receptacle 136 is in pocket 140B). Image capture device 128 has a field of view sufficient to subsequently capture image 152C (as sample rack 112 is further inserted within sample bay 102) that includes (1) fiducial machine-readable mark 150C on a bottom side of pocket 140C, and (2) machine-readable mark 147 on sample receptacle 136 in pocket 140C (or machine-readable mark 158 if no sample receptacle 136 is in pocket 140C). Image capture device 128 can subsequently capture similar images of fiducial machine-readable marks 150D, 150E, etc. and machine-readable marks 147 on sample receptacles 136 in pockets 140D, 140E, etc (or machine-readable marks 158 if no sample receptacles 136 are in pocket 140D, 140E, etc.).

Image capture device 128 can be configured to have a working distance range that includes each lane defined by sample bay 102 within housing 114 along which sample racks 112 move.

Sample assay instrument 100 can include a processor configured to process images captured by image capture device 128 to associate information contained in machine-readable marks 147 on each sample receptacle 136 on sample rack 112 with a specific location, for example, with a specific pocket 140, on sample rack 112. For example, the processor can process a captured image to identify at least one fiducial machine-readable mark 150 in the image. And then based on the known, predetermined position of a respective machine-readable mark 147 on a sample receptacle 136 relative to the identified fiducial machine-readable mark 150, the processor can identify and decode the respective machine-readable mark 147 on a respective sample receptacle 136. The processor can then associate information decoded from the respective machine-readable mark 147 with a specific location or pocket on sample rack 112 that is known to be associated with the identified fiducial machine-readable mark 150 in the image.

The processor can also save, into a memory of sample assay instrument 100, this association of information decoded from the respective machine-readable mark 147 with a specific location or pocket on sample rack 112 in some embodiments.

In some embodiments, for example, the processor determines if an image captured by image capture device 128 includes a fiducial machine-readable mark 150. In some embodiments, the processor processes the entire captured image to determine the presence of a fiducial machine-readable mark 150. In other embodiments, the processor processes only a portion of the captured image known to include fiducial machine-readable marks 150 to determine the presence of a fiducial machine-readable mark 150 in the captured image.

If the captured image does not include a fiducial machine-readable mark 150, the processor starts processing the next captured image.

If the captured image does include a fiducial machine-readable mark 150, the processor determines if the captured image includes a machine-readable mark at a known position relative to the identified fiducial machine-readable mark 150 in the captured image that corresponds to a position at which a machine-readable mark 147 on sample receptacle 136 would be if a sample receptacle 136 is in the pocket 140 associated with the identified fiducial machine-readable mark 150. In some embodiments, the processor processes the entire captured image to determine whether a machine-readable mark is at the known relative position. In other embodiments, the processor processes only a portion of the captured image that includes the known relative position to determine whether a machine-readable mark is at the known relative position. If the captured image does include a machine-readable mark 147 at the known relative position, the processor decodes the machine-readable mark 147 and associates the decoded information with a specific location or pocket on sample rack 112 that is known to be associated with the identified fiducial machine-readable mark 150 in the captured image. The processor can then store this association in a memory of sample assay instrument 100. Then the processor can start processing the next captured image, repeating the above steps.

If the captured image does not include a machine-readable mark 147 at the known position, the processor determines if the captured image includes a machine-readable mark at a known position relative to the identified fiducial machine-readable mark 150 in the captured image that corresponds to a position at which a machine-readable mark 158 would be if a receptacle 136 was not in the pocket 140 associated with the identified fiducial machine-readable mark 150. If the captured image does include a machine-readable mark 158, the processor starts processing the next captured image, repeating the above steps. In some embodiments, the processor processes the entire captured image to determine whether a machine-readable mark 158 is at the known relative position. In other embodiments, the processor processes only a portion of the captured image that includes the known relative position to determine whether a machine-readable mark 158 is at the known relative position.

For example, referencing either FIG. 5 or FIG. 8, the processor processes captured image 152A and determines, for example, by processing a portion of image 152A or the entire image 152A, that image 152A includes a fiducial machine-readable mark 150A. The processor then determines, for example, by processing the entire image 152A or a portion of image 152A, that the captured image 152A includes a machine-readable mark 147 at a known position relative to the identified fiducial machine-readable mark 150A in the captured image 152A that corresponds to a position at which a machine-readable mark 147 on sample receptacle 136 would be if a receptacle 136 is in pocket 140A associated with the identified fiducial machine-readable mark 150A. Next the processor decodes the machine-readable mark 147 in image 152A and associates the decoded information with a specific location or pocket on sample rack 112 that is known to be associated with the identified fiducial machine-readable mark 150 in captured image 152A. The processor can then store this association in a memory of sample assay instrument 100. Then the processor can start processing the next captured image 152B repeating the above steps.

In another processing embodiment, the processor processes each image captured by image capture device 128 to identify each machine-readable mark within the captured image 152. Next, the processor determines if any one of the identified machine-readable marks in the captured image is a fiducial machine-readable mark 150 on sample rack 112. If the identified machine-readable marks in the captured image includes a fiducial machine-readable mark 150, the processor then determines if any of the identified machine-readable marks in the captured image is located at a known position relative to the identified machine-readable mark(s) 150 in the captured image that corresponds to a position at which a machine-readable mark 147 on receptacle 136 would be if a receptacle 136 is in the corresponding pocket 140 associated with the identified fiducial machine-readable mark(s) 150. If the identified machine-readable marks in captured image 152 includes a machine-readable mark 147 at the know position relative to the identified machine-readable mark(s) 150 in the captured image, the processor decodes the machine-readable mark 147 and associates the decoded information within the machine-readable mark 147 with a specific location or pocket 140 that corresponds to the identified machine-readable mark(s) 150. The processor can then store this association in a memory of sample assay instrument 100. If the identified machine-readable marks in the captured image does not include a machine-readable mark 158 at the known position relative to the identified machine-readable mark(s) 150 in the captured image 152 that corresponds to a position at which either a machine-readable mark 147 on receptacle 136 would be if a receptacle 136 is in the corresponding pocket 140, the processor then determines if any of the identified machine-readable marks in the captured image is located at a known position relative to the identified machine-readable mark(s) 150 in the captured image that corresponds to a position at which a machine-readable mark 158 in corresponding empty pocket 140 associated with the identified fiducial machine-readable mark(s) 150. If the identified machine-readable marks in captured image 152 includes a machine-readable mark 158 at the known position relative to the identified machine-readable mark(s) 150 in the captured image, the processor decodes the machine-readable mark 158 and associates an empty status with the specific location or pocket 140 that corresponds to the identified machine-readable mark(s) 150. The processor can then store this association in a memory of sample assay instrument 100. The processor can repeat these steps for each captured image 152.

In some embodiments, sample bay 102 is configured such that sample racks 112 are manually inserted within housing 114 of sample bay 102. In this disclosure, "manually inserted," "manually moved," or similar phrases mean that sample racks 112 are inserted or moved without using automated or electrical device components. That is, sample racks 112 are inserted or moved within housing 114 along the defined lanes using only the user's hands. When sample racks 112 are manually moved, sample racks 112 can move at a high speed that exceeds 100 mm/sec, for example, speeds greater than 300 mm/sec, 500 mm/sec, 600 mm/sec, or 1000 mm/sec, in some embodiments.

In other embodiments, sample bay 102 is configured to automatically move sample rack 112 within housing 114 of sample bay 102. For example, sample bay 102 can include an automated actuator that moves sample racks 112 within housing 114 of sample bay 102 to a fully inserted position. In some embodiments, sample rack 112 is automatically moved within housing 114 at a known, constant speed.

Referencing FIG. 9, to insert a sample rack 112 within housing 114 of sample bay 102, a user aligns sample rack 112 with guides 123 on base 116. The user then moves sample rack 112 in a direction 158 (as shown in FIG. 9) along a lane defined by guides 123 from a first, initial position to a second, fully inserted position within housing 114 of sample bay 102. As shown FIG. 9, sample receptacles 136 are placed in sample rack 112 such that machine-readable marks 147 are aligned with the openings defined by the dividing walls 142 that separate adjacent pockets 140 from each other. Accordingly, machine-readable marks 147 are visible to image capture device 128 through opening 132 defined in side wall 120 of housing 114. Thus, as sample rack 112 moves from the initial position to the fully inserted position, image capture device 128 can read machine-readable marks 147 on each sample receptacle 136 on sample rack 112, as well as pocket identifying fiducial machine-readable marks 150, rack identifying machine-readable mark 148, cover identifying machine-readable mark 156, and empty-pocket identifying machine-readable mark 158.

In some embodiments, image capture device 128 has a field of view configured to capture image 152. Image capture device 128 can have a working distance range large enough to include each lane defined in housing 114, along which sample racks 112 move in some embodiments.

In some embodiments, the image capture device 128 has a sufficient depth of field such that each of fiducial machine-readable marks 150, machine-readable marks 147 on each sample receptacle 136, rack identifying machine-readable mark 148, cover identifying machine-readable mark 156, and empty-pocket identifying machine-readable mark 158 are sufficiently in focus in the captured images to allow the processor to process the captured images as described above. For example, fiducial machine-readable marks 150, rack identifying machine-readable mark 148, and cover identifying machine-readable mark 156 are substantially located in the same plane as shown in FIG. 9, but machine-readable marks 147 on each sample receptacle 136 and empty-pocket identifying machine-readable mark 158 can be offset from that plane in a direction away from image capture device 128 due to the location on receptacle 136 and the wall of pocket 140 on which machine-readable marks 147 and empty-pocket identifying machine-readable mark 158, respectively, are located in some embodiments. In some embodiments, image capture device 128 can have a sufficient depth of field, for example, such that each of these machine-readable marks are in sufficient focus in the captured image to allow for the above described processing. In some embodiments, the depth of focus can be about 1 inch, which can be about the diameter of pocket 140 in some embodiments.

In some embodiments, image capture device 128 is a camera. Exemplary cameras include a charge-coupled device (CCD) camera or complementary metal-oxide-semiconductor (CMOS) camera. In some embodiments, image capture device 128 captures a plurality of images 152 at a rate sufficient to acquire an image of machine-readable marks 147 on each sample receptacle 136, fiducial machine-readable marks 150, rack identifying machine-readable mark 148, cover identifying machine-readable mark 156, and empty-pocket identifying machine-readable mark 158 when on sample rack 112 is moving at a rate up to at least 1000 mm/sec, including for example 100 mm/sec, 300 mm/sec, 500 mm/sec, and 600 mm/sec. For example, in some embodiments, image capture device 128 captures an image 152 at a rate of at least 20 Hz, such as 25 Hz, 35 Hz, 50 Hz or 60 Hz.

Referencing FIG. 9, as sample rack 112 is inserted into sample bay 102 along a lane defined by guides 123 (and in direction 158), image capture device 128 acquires a plurality of images of sample rack 112 and receptacles 136 contained therein as it passes through the field of view of image capture device 128. For example, the acquired images 152 can include machine-readable marks 147 on each sample receptacle 136, fiducial machine-readable marks 150, rack identifying machine-readable mark 148, cover identifying machine-readable mark 156, and empty-pocket identifying machine-readable mark 158. In some embodiments, the acquired images 152 are transmitted to the processor that is configured to process the acquired images as described above. In some embodiments, the processor is coupled to or disposed in housing 114. In some embodiments, this image processing by the processor occurs while the sample rack is being inserted within housing 114. In other embodiments, this image processing by the processor occurs after sample rack 112 is fully inserted into housing 114 of sample bay 102.

In some embodiments, the processor is also configured to activate the light source when sample rack 112 each time an image 152 is captured. Using the light source when acquiring image 152 can further reduce the necessary performance requirement(s) of image capture device 128.

Although the above described embodiments include a sample rack 112 and sample receptacles 136, the embodiments are not limited to sample racks 112 and sample receptacles 136. For example, these embodiments can be applied to other racks and fixtures of sample assay instrument 100 that hold reagent containers or other processing consumables. Accordingly, the above described embodiments can be used to determine the position of the reagent containers or other processing consumables relative to the rack or fixture on which the respective reagent containers or other processing consumables are placed.

Although the above described embodiments include an image capture device 128 that is fixedly coupled to sample bay 102, the disclosed embodiments are not limited to fixed readers 128. For example, these embodiments can be applied using a handheld reader that the user manually operates. Such hand-held embodiments can help address user variability that may result in receptacles 136 being scanned non-sequential order.

Some embodiments are implemented via control and computing hardware components, user-created software, data input components, and data output components. Hardware components include, for example, the processor, such as a microprocessor or computer, configured to effect computational and/or control steps by receiving one or more input values, executing one or more algorithms stored on non-transitory machine-readable media (e.g., software) that provide instruction for manipulating or otherwise acting on the input values, and output one or more output values. Such outputs may be displayed or otherwise indicated to an operator for providing information to the operator, for example information as to the status of the instrument or a process being performed thereby, or such outputs may comprise inputs to other processes and/or control algorithms. Data input components comprise elements by which data is input for use by the control and computing hardware components. Such data inputs may comprise image capture devices, positions sensors, motor encoders, as well as manual input elements, such as graphic user interfaces, keyboards, touch screens, microphones, switches, manually-operated scanners, voice-activated input, etc. Data output components may comprise hard drives or other storage media, graphic user interfaces, monitors, printers, indicator lights, or audible signal elements (e.g., buzzer, horn, bell, etc.). In some embodiments, the processor can comprise a single module that performs image processing and system control. In other embodiments, the processor comprises a plurality of modules that perform discrete processing and control steps. In some embodiments, the processor can be a component of image capture device 128 that processes (for example, post-processing) images stored in a buffer of image capture device 128.

Software comprises instructions stored on non-transitory computer-readable media which, when executed by the control and computing hardware, cause the control and computing hardware to perform one or more automated or semi-automated processes. In some embodiments, the software for image processing is stored in memory on image capture device 128, for example. In some embodiments, the software for image processing is stored in external memory in communication with the processor.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A sample instrument comprising:
    a moveable support configured to move from a first position to a second position, the moveable support defining a first pocket configured to receive a first object having a first machine-readable mark, and defining a second pocket configured to receive a second object having a second machine-readable mark, the moveable support comprising a first fiducial machine-readable mark containing information that identifies a location of the first fiducial machine-readable mark and a second fiducial machine-readable mark containing information that identifies a location of the second fiducial machine-readable mark; and
    an image capture device having a field of view that captures a first image including the first fiducial machine-readable mark and, when the first object is received within the first pocket, the first machine-readable mark of the first object, and captures a second image as the moveable support moves from the first position to the second position that includes the second fiducial machine-readable mark and, when the second object is received within the second pocket, the second machine-readable mark of the second object; and
    a processor configured to
        decode the first machine-readable mark and the first fiducial machine-readable mark in the first image,
        associate information decoded from the first machine-readable mark with a first location on the moveable support having a predetermined association with the first fiducial machine-readable mark,
        decode the second machine-readable mark and the second fiducial machine-readable mark in the second image, and
        associate information decoded from the second machine-readable mark with a second location on the moveable support having a predetermined association with the second fiducial machine-readable mark.

2. The sample instrument of claim 1, wherein the first object has different dimensions than the second object.

3. The sample instrument of claim 1, wherein:
    the moveable support is a sample rack, a reagent drawer, or a consumable drawer;
    the first object is a first sample receptacle, a first reagent container, or a first consumable; and
    the second object is a second sample receptacle, a second reagent container, or a second consumable.

4. The sample instrument of claim 1, wherein:
    the first fiducial machine-readable mark is a first one- or two-dimensional barcode; and
    the second fiducial machine-readable mark is a second one- or two-dimensional barcode.

5. The sample instrument of claim 4, wherein the first fiducial machine-readable mark is different from the second fiducial machine-readable mark.

6. The sample instrument of claim 1, wherein:
    the first fiducial machine-readable mark is below, above, or to a lateral side of the first pocket; and
    the second fiducial machine-readable mark is below, above, or to a lateral side of the second pocket.

7. The sample instrument of claim 1, wherein the processor is further configured to
    identify the first machine-readable mark in the first image based on a predetermined position of the first machine-readable mark in the first image relative to the position of the first fiducial machine-readable mark in the first image; and
    identify the second machine-readable mark in the second image based on a predetermined position of the second machine-readable mark in the second image relative to the position of the second fiducial machine-readable mark in the second image.

8. The sample instrument of claim 1, wherein the processor is further configured to
    identify the first machine-readable mark in the first image by processing only a portion of the first image that includes the predetermined position of the first machine-readable mark in the first image relative to the position of the first fiducial machine-readable mark in the first image; and
    identify the second machine-readable mark in the second image by processing only a portion of the second image that includes the predetermined position of the second machine-readable mark in the second image relative to the position of the second fiducial machine-readable mark in the first image.

9. The sample instrument of claim 1, wherein the processor is further configured to
    identify the first machine-readable mark in the first image by processing the entire first image; and
    identify the second machine-readable mark in the second image by processing the entire second image.

10. The sample instrument of claim 1, wherein the processor is further configured to
   process only a predetermined portion of the first image to identify the first fiducial machine-readable mark in the first image; and
   process only a predetermined portion of the second image to identify the second fiducial machine-readable mark in the second image.

11. The sample instrument of claim 1, wherein the processor is further configured to
   process the entire first image to identify the first fiducial machine-readable mark in the first image; and
   process the entire second image to identify the second fiducial machine-readable mark in the second image.

12. The sample instrument of claim 1, wherein the sample instrument comprises a sample assay instrument.

13. The sample instrument of claim 1, wherein the sample instrument comprises a sample processing instrument.

14. The sample instrument of claim 1, wherein the image capture device comprises a camera.

15. The sample instrument of claim 3, wherein:
   the moveable support comprises the reagent drawer;
   the first object comprises the first reagent container; and
   the second object comprises the second reagent container.

16. The sample instrument of claim 3, wherein:
   the moveable support comprises the consumable drawer;
   the first object comprises the first consumable; and
   the second object comprises the second consumable.

17. The sample instrument of claim 4, wherein:
   the first machine-readable mark comprises the first one-dimensional barcode; and
   the second machine-readable mark comprises the second one-dimensional barcode.

18. The sample instrument of claim 17, wherein the first machine-readable mark is different from the second machine-readable mark.

19. The sample instrument of claim 6, wherein:
   the first fiducial machine-readable mark is above the first pocket; and
   the second fiducial machine-readable mark is above the second pocket.

20. The sample instrument of claim 6, wherein:
   the first fiducial machine-readable mark is positioned to the lateral side of the first pocket; and
   the second fiducial machine-readable mark is positioned to the lateral side of the second pocket.

21. The sample instrument of claim 6, wherein:
   the first fiducial machine-readable mark is below the first pocket; and
   the second fiducial machine-readable mark is below the second pocket.

22. The sample instrument of claim 1, wherein the moveable support manually moves from the first position to the second position.

* * * * *